(12) United States Patent
Moazzami et al.

(10) Patent No.: US 10,888,508 B1
(45) Date of Patent: Jan. 12, 2021

(54) MULTI-FUNCTIONAL COOLANT FOR DENTISTRY USE

(71) Applicants: Saied Mostafa Moazzami, Upland, CA (US); Hosein Orafaee, Mashhad (IR)

(72) Inventors: Saied Mostafa Moazzami, Upland, CA (US); Hosein Orafaee, Mashhad (IR)

(*) Notice: Subject to any disclaimer, the term of this patent is extended or adjusted under 35 U.S.C. 154(b) by 0 days.

(21) Appl. No.: 16/014,433

(22) Filed: Jun. 21, 2018

(51) Int. Cl.
| A61K 9/08 | (2006.01) |
| A61K 45/06 | (2006.01) |
| A61K 8/44 | (2006.01) |
| A61K 8/49 | (2006.01) |
| A61K 8/368 | (2006.01) |
| A61Q 11/00 | (2006.01) |
| A61C 1/00 | (2006.01) |

(52) U.S. Cl.
CPC .............. *A61K 8/44* (2013.01); *A61K 8/368* (2013.01); *A61K 8/4973* (2013.01); *A61K 8/4993* (2013.01); *A61Q 11/00* (2013.01); *A61C 1/0084* (2013.01); *A61K 2800/244* (2013.01); *A61K 2800/524* (2013.01); *A61K 2800/596* (2013.01)

(58) Field of Classification Search
CPC .. A61K 2300/00; A61K 45/06; A61K 9/0053; A61K 9/0056; A61K 9/08; A61Q 11/00
See application file for complete search history.

(56) References Cited

U.S. PATENT DOCUMENTS

| 5,032,388 A * | 7/1991 | Tikkanen | A61K 8/44 424/49 |
| 5,310,542 A * | 5/1994 | Au | A61Q 11/00 424/49 |
| 2006/0286044 A1* | 12/2006 | Robinson | A61K 8/345 424/49 |
| 2007/0258913 A1* | 11/2007 | Rossel | A61K 31/122 424/49 |
| 2008/0193912 A1* | 8/2008 | Fong | A61P 43/00 435/2 |
| 2010/0135924 A1* | 6/2010 | Deckner | A61K 8/922 424/49 |
| 2014/0219933 A1* | 8/2014 | Piergallini | A61K 45/06 424/56 |
| 2017/0312195 A1* | 11/2017 | Fei | A61K 8/345 |

* cited by examiner

*Primary Examiner* — Tracy Liu
(74) *Attorney, Agent, or Firm* — Plager Schack LLP; Mark H. Plager; Kara Verryt

(57) ABSTRACT

A multifunctional dental composition may include polyoxyethylene sorbitan monooleate; sorbitan monooleate; benzoate sodium; distilled water; and ethylene diamine tetra acetic acid. For dental use, the required hydrophilic/lipophilic balance of the composition may be 7; and a critical micellar concentration of the composition may be 0.5%. The dental composition may be applied in a manner similar to how tap water is conventionally used, and the composition may be delivered to the dental unit system using various methods.

1 Claim, 2 Drawing Sheets

MULTI-FUNCTIONAL COOLANT FOR DENTISTRY USE

BACKGROUND

The embodiments herein relate generally to dental compositions, and more particularly, to a multi-functional dental coolant that may be used, specifically, for cooling dental cutting burs/drills while simultaneously removing the cutting related particles and consequently the smear layer.

In dentistry, rotating burs, drills, and working heads of instruments, as well as the cut tooth structure and dental materials, need cooling and cleaning. Conventionally, cooling is done by spraying tap water from the head of high or low-speed handpieces on burs/drills in cavity preparation or heads of other dental instruments.

Cutting/drilling the tooth structure during cavity preparation with burs/drills, which is cooled by tap water as mentioned above, generates a smear layer, which decreases Surface Free Energy (SFE) of enamel/dentin that interferes with composite-tooth bonding and increases the potential of micro-leakage. However, the smear layer cannot be completely removed using tap water spray while cutting. Currently, the smear layer is removed and modified with total-etched and self-etched approaches respectively.

Because cooling, cleaning, and removing the smear layer are performed separately, such procedures require multiple clinical steps, which take time and produces technique sensitivities.

Therefore, what is needed is a cooling composition that provides for cooling, cleaning, and removing the smear layer simultaneously.

SUMMARY

Some embodiments of the present disclosure include a multifunctional dental composition for use as a dental coolant and a method of applying the multifunctional dental composition. The composition and application thereof together provide an alternative approach to cope with the smear layer through cooling dental cutting burs/drills, as well as simultaneously removing the cut related particles and consequently the smear layer during cutting/drilling or cavity preparation. The composition may include polyoxyethylene sorbitan monooleate; sorbitan monooleate; benzoate sodium; distilled water; and ethylene diamine tetra acetic acid. For dental use, the hydrophilic/lipophilic balance of the composition may be 7; and a needed critical micellar concentration of the composition may be 0.5%.

The composition of the present disclosure may be used in a manner like how tap water spray is conventionally used. The composition may be delivered to the dental unit system through different ways. It may function physicochemically to cool and remove the smear layer at the same time as cutting to provide a higher level of SFE in total-etch approach. It may also provide the same level of bond strength that occurs in total-etch and self-etch approaches.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

In the following detailed description of the invention, numerous details, examples, and embodiments of the invention are described. However, it will be clear and apparent to one skilled in the art that the invention is not limited to the embodiments set forth and that the invention can be adapted for any of several applications.

The composition of the present disclosure may be used as a multi-functional dental coolant and may comprise the following elements. This list of possible constituent elements is intended to be exemplary only, and it is not intended that this list be used to limit the composition of the present application to just these elements. Persons having ordinary skill in the art relevant to the present disclosure may understand there to be equivalent elements that may be substituted within the present disclosure without changing the essential function or operation of the composition.

a. Hydrophilic Surfactant
b. Lipophilic Surfactant
c. Ethylene Diamine Tetra Acetic Acid
d. Benzoate Sodium
e. Distilled Water The various elements of the composition of the present disclosure may be related in the following exemplary fashion. It is not intended to limit the scope or nature of the relationships between the various elements and the following examples are presented as illustrative examples only.

Figure 1:
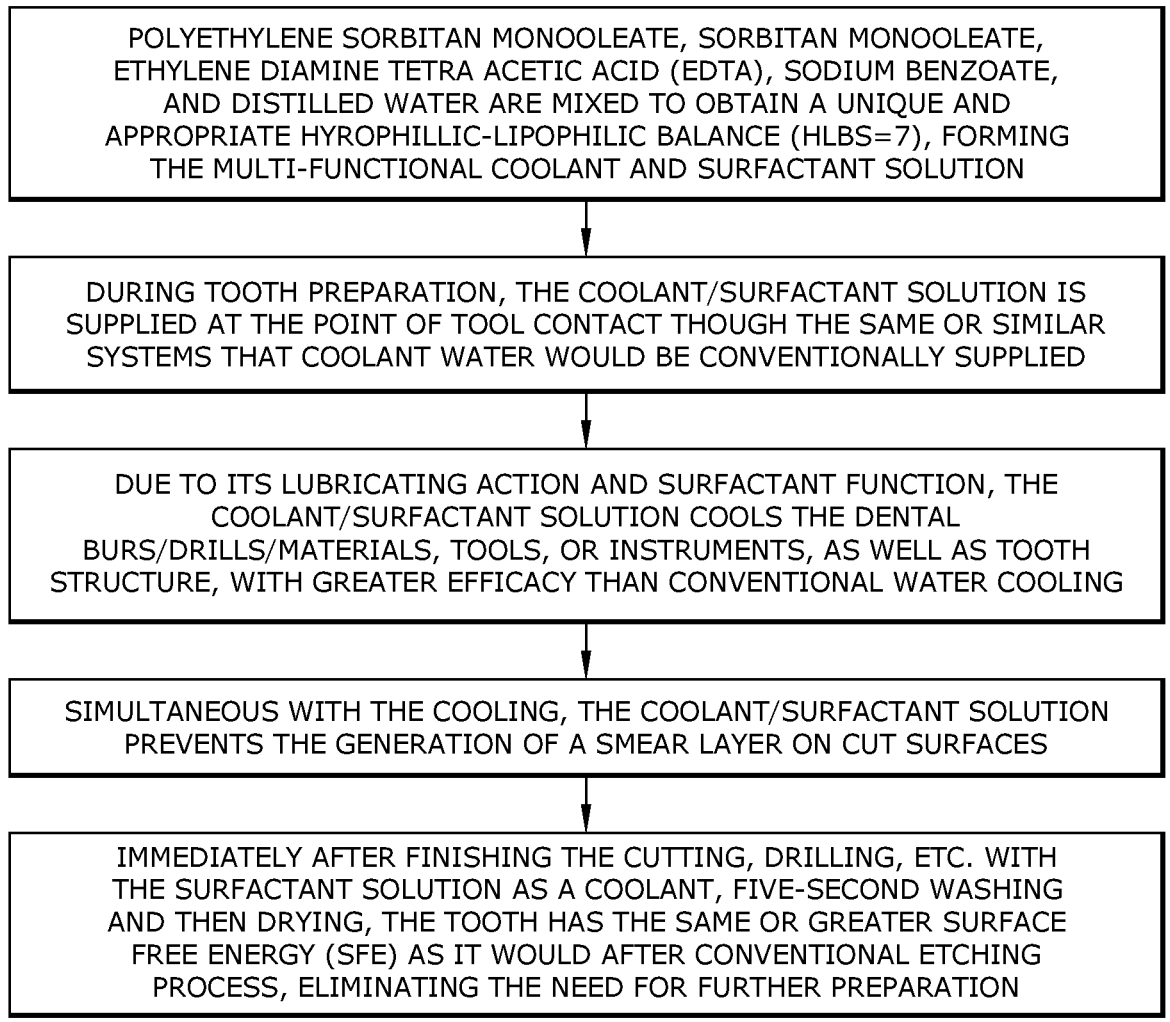
FIG. 1 is a flow chart describing preparation and use of the composition of the present disclosure.
Figure 2:
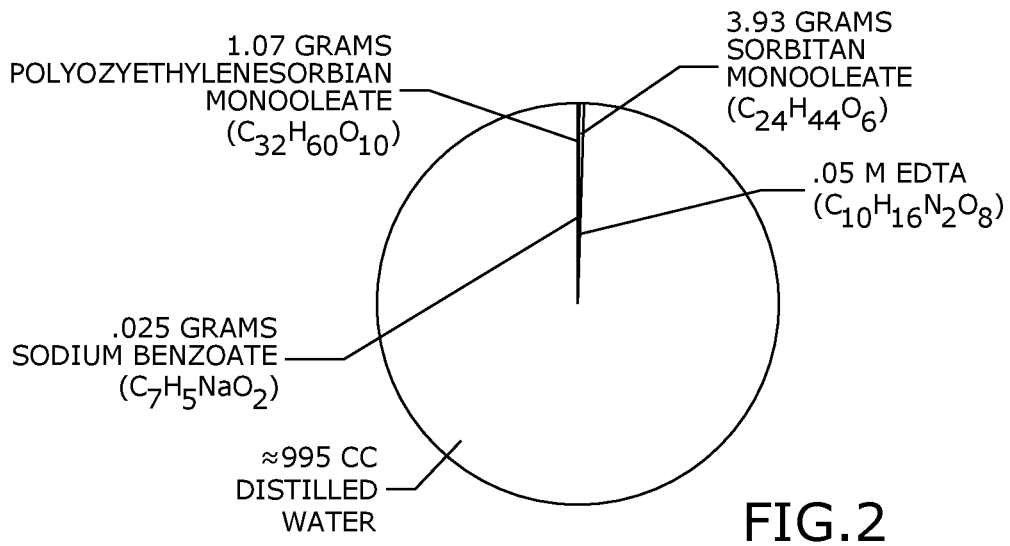
FIG. 2 is a schematic view of an exemplary formulation of the composition of the present disclosure.
Figure 3:
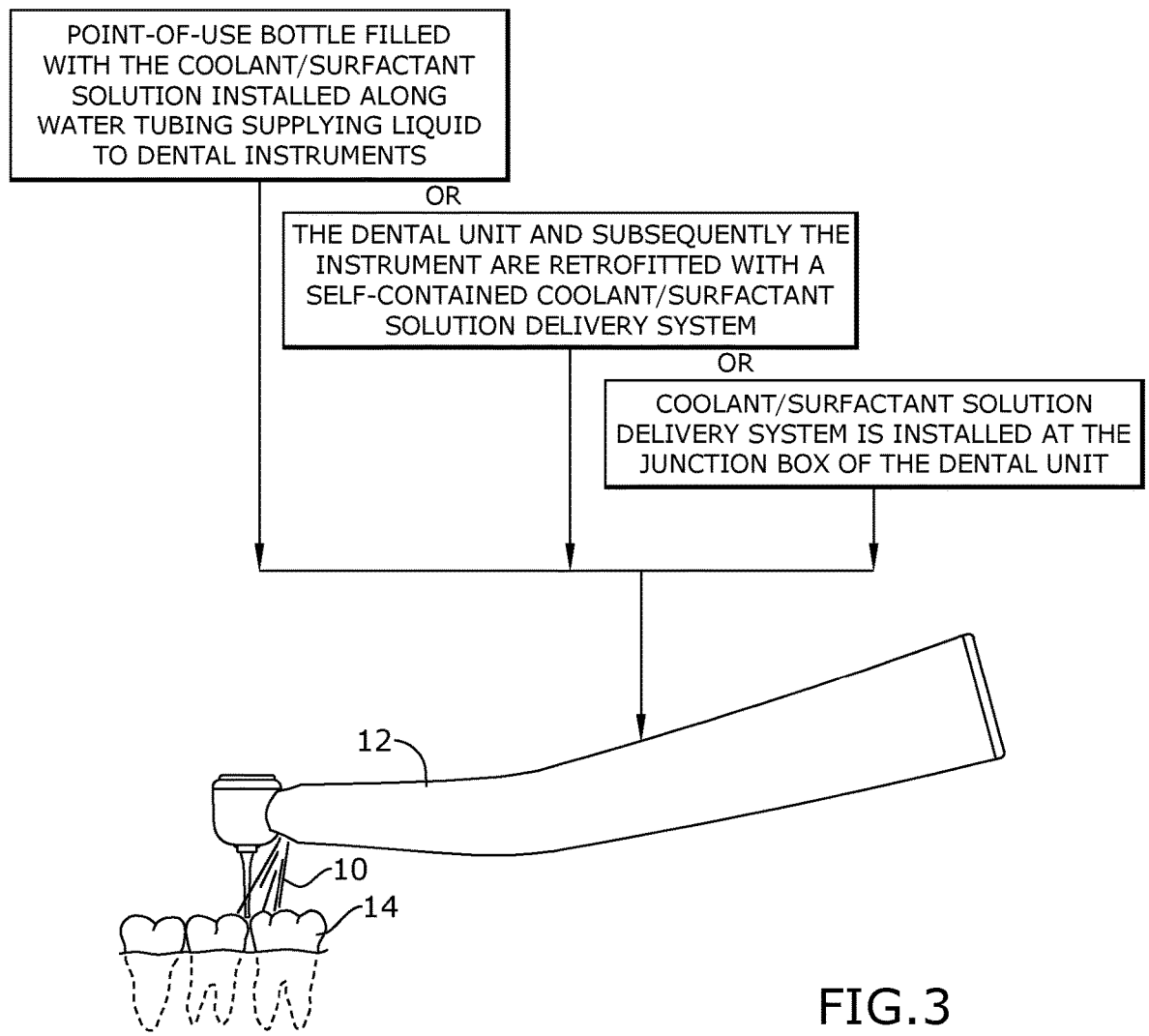
FIG. 3 is a schematic view of an exemplary solution delivery method of the composition of the present disclosure.

By way of example, and referring to FIGS. 1-3, some embodiments of the present disclosure include a multi-functional dental composition 10 for cooling dental instruments and removing a smear layer on a tooth 14 simultaneously, the multi-functional dental composition 10 comprising a mixture of surfactants, ethylene diamine tetra acetic acid (EDTA), such as 0.5 molar EDTA, a preservative, and a cooling agent.

In embodiments, the surfactants may comprise non-ionic surfactants, such as a mixture of a hydrophilic surfactant and a lipophilic surfactant. For example, the hydrophilic surfactant may comprise polyoxyethylene sorbitan monooleate (TWEEN 80), and the lipophilic surfactant may comprise sorbitan monooleate (SPAN 80). The hydrophilic/lipophilic balance (HLB) may be 7 and a Critical Micellar Concentration (CMC), which may be 0.5%.

The preservative may be benzoate sodium, and the cooling agent may be distilled water.

A specific embodiment of the composition of the present disclosure may comprise about 995 cc of distilled water ($H_2O$), about 0.025 g sodium benzoate ($C_7H_5NaO_2$), about 1.07 g polyoxyethylene sorbitan monooleate ($C_{32}H_{60}O_{10}$), about 3.93 g sorbitan monooleate ($C_{24}H_{44}O_6$), and about 0.05M ethylene diamine tetra acetic acid (EDTA) ($C_{10}H_{16}N_2O_8$) in 1000 cc.

To use the composition of the present disclosure, it may be used in a manner similar to how tap water is conventionally used. For example, as shown in FIG. 3, the composition 10 may be sprayed onto a tooth 14 using a handpiece 12, such as a high-speed handpiece, low-speed handpieces, straight and contra-angle handpieces, endodontic rotary instruments, ultrasonic scalers, air abrasion systems, sonic instruments, lasers, and surgical handpieces. The composition may be delivered to the dental unit system through the following ways:

(a) A point of use bottle: A reservoir (bottle) filled with the composition, wherein the reservoir attaches to the dental unit waterline and can be adjusted between the dental instruments and the waterline tubes/pipes, which can isolate them from the municipal water supply. The composition may be added manually, and the reservoir may be refilled. The composition may also be delivered through any concentrated solution, gel, powder, or tablet, which may be added to the defined amount of distilled water.

(b) A larger container may be connected to the waterway that is just reaching the dental instruments.

(c) A system may be installed that allows articulated delivery of the composition to the tap water at a junction box.

(d) A conventional syringe method may be used to use the solution as an irrigation solution in endodontics, periodontics, surgery and implant dentistry.

More particularly, as shown in FIG. 1, making and using the composition may comprise mixing polyethylene sorbitan monooleate, sorbitan monooleate, EDTA, sodium benzoate, and distilled water to obtain the multi-functional composition having an HLB of 7 and CMC of 0.5%. During tooth preparation, the composition may be supplied at the point of tool contact through the same or similar systems that coolant water would be conventionally supplied. Due to its lubricating action and surfactant function, the composition may cool the dental burs/drills/materials, tools, or instruments, as well as tooth structure, with greater efficacy than conventional water cooling. Simultaneously with the cooling, the coolant/surfactant solution may prevent the generation of a smear layer on cut surfaces. Immediately after finishing the cutting, drilling, etc. with the composition of the present disclosure as a coolant, five-second washing and then drying, the tooth may have the same or greater surface free energy (SFE) as it would after conventional etching processes, eliminating the need for acid etching for further preparation of the dental substrate.

Because of the composition of the coolant of the present disclosure, it may be multi-functional. Not only may it remove the smear layer from the dentin surface of cut tooth structures, thus being effective in adhesion to the tooth, but it may simultaneously act as a cooling, lubricating, and cleaning agent for the cut tooth structure and dental material, as well as the burs, drills, and head of other mechano-physical instruments.

EXAMPLES AND COMPARATIVE EXAMPLES

Study 1: Formulations of Water-Based Surfactant/Coolant Solutions Were Developed. The composition included TWEEN 80 (polyoxyethylene sorbitan monooleate) and SPAN 80 (sorbitan monooleate), which were prepared if 0.5% total concentration of the mixed surfactants in distilled water (5 g/1000 mL) to obtain five different HLB levels ranging from 6 to 10. TWEEN 80 has an HLB of 15.8, and SPAN 80 has an HLB of 4.6. Due to these HLB values and the targeted HLBs and total concentrations of the solution, the ingredients were combined in the proportions and weights (in grams) as described in Table 1 using allegation medical to mix the ingredients.

TABLE 1

| Composition | HLB | Total Concentration | TWEEN 80/SPAN 80 Ratio | TWEEN 80 (grams) | SPAN 80 (grams) | EDTA (Molar) |
|---|---|---|---|---|---|---|
| 1 | 6 | 0.5% | 1.4/9.8 | 0.62 | 4.38 | N/A |
| 2 | 7 | 0.5% | 2.4/8.8 | 1.07 | 3.93 | N/A |
| 3 | 8 | 0.5% | 3.4/7.8 | 1.51 | 3.49 | N/A |
| 4 | 9 | 0.5% | 4.4/6.8 | 1.96 | 3.04 | N/A |
| 5 | 10 | 0.5% | 5.4/5.8 | 2.41 | 2.59 | N/A |
| 6 | 7 | 2.0% | 2.4/8.8 | 4.28 | 15.72 | N/A |
| 7 | 7 | 0.5% | 2.4/8.8 | 1.07 | 3.93 | 0.5 |
| 8 | 7 | 0.5% | 2.4/8.8 | 1.07 | 3.93 | 0.1 |
| 9 | 7 | 0.5% | 2.4/8.8 | 1.07 | 3.93 | 0.05 |

Step 1: Surface Free Energy (SFE) Measurement: To prepare a very flat and horizontal dentinal surface for measuring SFE, 88 extracted sound third molar teeth were carefully cut from the base level of the cusps, at occlusal one-third, using a high-speed handpiece with a long diamond bur and tap water spray. 56 of the prepared teeth were randomly divided into seven groups of eight teeth each in two controls and five testing groups. To stimulate real cutting manner, dentinal surfaces in all groups were cut and prepared again using a high-speed handpiece with a new long diamond fissure bur for 5 seconds while test composition was sprayed for each defined group. Washing with air/tap water spray for 5 seconds and drying were done as usual. The positive control group ($C^+$) had the same bur cutting procedure, but with tap water spray alone as the conventional coolant. Then washing and drying were done as usual. In the negative control group ($C^-$), dentinal flat surfaces received bur cutting with tap water spray as the conventional coolant, drying, and acid etching with 37% phosphoric acid for 10 seconds. Washing and drying were done as manufacturer's instruction. See Table 2 below.

TABLE 2

| Step | Controls and Testing Group | Surface Treatment | HLB | Surfactant/ Coolant Composition | Abbreviation |
|---|---|---|---|---|---|
| 1 | Positive Control | — | — | Tap water spray | $C^+$ |
| 1 | Negative Control | 37% phosphoric acid gel for 10 sec. | — | Tap water spray | $C^-$ |
| 1 | Testing | Composition 1 (0.5% concentration) | 6 | $S_1$ spray | $S^1$ |
| 1 | Testing | Composition 2 (0.5% concentration) | 7 | $S_2$ spray | $S^2$ |
| 1 | Testing | Composition 3 (0.5% concentration) | 8 | $S_3$ spray | $S^3$ |
| 1 | Testing | Composition 4 (0.5% concentration) | 9 | $S_4$ spray | $S^4$ |
| 1 | Testing | Composition 5 (0.5% concentration) | 10 | $S_5$ spray | $S^5$ |
| 2 | Testing | Composition 2 (2% concentration) | 7 | $S_6$ spray | $S^6$ |
| 3 | Testing | Composition 2 + 0.5M EDTA | 7 | $S_7$ spray | $S^7$ |
| 3 | Testing | Composition 2 + 0.1M EDTA | 7 | $S_8$ spray | $S^8$ |
| 3 | Testing | Composition 2 + 0.05M EDTA | 7 | $S_9$ spray | $S^9$ |

The SFE of the dentin was determined using two different reference liquids [triple-distilled water (as a best polar reference liquid) and methylene iodine (as a best non-polar reference liquid)] in each prepared tooth after repeating the mentioned procedures respectively. At the time of applying the reference liquids, a video was taken. The contact angle measurement was done on the snapshot photos that were taken from the 6$^{th}$ second of each video using Auto-CAD software.

Finally, the angle values were incorporated into the following geometric Paddy equation [$\gamma L$ (Cos $\Theta$+1)=2 ($\gamma Sd\gamma Ld$)1/2+2($\gamma Sp\gamma Lp$)1/2] to get the SFE (mj/m$_2$) of dentin.

To find the best surfactant/solution (composition) in terms of SFE, three-way ANOVA and Duncan showed that surfactant/solution used in group S$^2$ produce the highest SFE. See Table 3.

TABLE 3

| Groups | No. | SUBSET 1 (mJ/m$^2$) | SUBSET 2 (mJ/m$^2$) |
|---|---|---|---|
| S$_4$ | 8 | 44.3250 | |
| S$_1$ | 8 | 47.4000 | |
| S$_5$ | 8 | 48.1250 | |
| S$_3$ | 8 | 56.2250 | 56.2250 |
| S$_2$ | 8 | 57.2750 | 57.2750 |
| C$^-$ | 8 | 57.8500 | 57.8500 |
| C$^+$ | 8 | | 72.8250 |
| Sig. | | .152 | .072 |

Step 2: Evaluating the Effect of Concentrations of Surfactant/Coolant Solution: Eight samples cooled with the Composition 2 with 2% concentration was considered as the S$^6$. The cutting procedures and SFE measurements were done in the same manner as in Step 1. Three-way ANOVA and Duncan showed no significant difference between S$^2$ and S$^6$ while SFE in S$^2$>S$^6$. See Table 4.

TABLE 4

| Groups | No. | SUBSET 1 (mJ/m$^2$) | SUBSET 2 (mJ/m$^2$) |
|---|---|---|---|
| S$_6$ | 8 | 56.2250 | |
| S$_2$ | 8 | 57.2750 | |
| C$^-$ | 8 | 57.8500 | |
| S$_9$ | 8 | 68.7250 | 68.7250 |
| S$_8$ | 8 | 70.3750 | 70.3750 |
| C$^+$ | 8 | | 72.8250 |
| S$_7$ | 8 | | 76.9750 |
| Sig. | | .051 | .235 |

Step 3: Effective Concentrations of EDTA: Three concentrations of EDTA (0.5, 0.1, and 0.05M) with S$^2$ were used to formulate another three surfactant/coolant solutions (compositions) for another three testing groups (S$^7$, S$^8$, and S$^9$, HLB=7, CMC=0.5%) with 8 samples in each. Three-way ANOVA and Duncan were done to find the effect of adding EDTA on SFE. The analysis showed that the best surfactant/coolant solution in terms of SFE, among all controls and testing groups was S$^7$. See Table 4 above.

Study 1: SEM Evaluation: A qualitative SEM survey was performed on negative and positive control groups, as well as group S$^2$ and group S$^7$ of Study 1. Three teeth from each selected group were prepared as their protocols. To fix dentinal surface characterization (and possibly the smear layer), their dentin surfaces were mummified using a layer of a bonding agent, which was cured for 10 seconds, layered by 2.0×2.0 mm polyethylene cylinder of the composite resin, and cured for 40 seconds. They were then sectioned using the diamond disc from the mid-both side, up to near the interface to make the sample being fractured perpendicular to the interface easily. Then a fractured surface was prepared for SEM analysis to the interfacial detection (presence or absence) of the smear layer.

In a selected sample of the C$^+$, smear layer was detected as a 6.0μ thickness with a white amorphous layer between resin and tooth surface. In a selected sample of the C$^-$, the absolute absence of smear layer demonstrates a firm contact between the tooth and adhesive resin, which indicates complete removal of smear layer with the 37% phosphoric acid application for 10 seconds. In group S$^2$, spot analysis revealed a very small number of particles containing calcium and phosphor at the tooth-adhesive interface. A white very thin layer was observed between adhesive and tooth into S$^7$ revealed calcium, phosphor, and silica content in the analysis.

Study 1: Results: The composition of the present disclosure (S$^7$) introduces a new coolant with smear layer removal function, as an alternative approach.

In step 1 of experimental study (Surface Free Energy Measurement), results showed that the best group in term of SFE level in groups S$^1$-S$^5$ (with surfactant/coolant alone), was group S$^2$ with HLB=7 (57.27 mj/m2) and CMC=0.5%. On the other hand, the results also showed that in the testing groups (S$^1$-S$^5$), the SFE level is only a little less than C$^-$ with no significant difference. In other words, C$^-$ and groups S$^1$-S$^5$ are placed in the same subset. This finding could be attributed to the possible remnants of surfactant/coolant molecules after 5 second washing time. Different soaps were used for preparation of dentin surface, and using soap decreases bond strength. Thus, the remnants of surfactant/coolant are possibly the reason for this decrease.

Comparison between S$^2$ (step 1) and S$^6$ (step 2) showed that increasing the surfactant/coolant solution concentration had no effect on SFE. As a matter of fact, surfactant bipolar molecules disperse in watery or oily solutions, but with a specific concentration, they make complexes called "Micelles," which provides the maximum characteristic for the surfactant. Each micelle is an aggregation of the surfactant bipolar molecules as a sphere suspended in the solution. This concentration at which these Micelles are formed called Critical Micellar Concentration (CMC). CMC increases the cleaning and chemical stability of the solution. Surfactants (TWEEN® 80 and Span® 80) used in this study at the Critical Micellar Concentration (CMC), which is considered 0.5%, has the maximum characteristic for the surfactant e.g. reduction of surface tension of distilled water.

Comparison between SFE of S$^7$, S$^8$, and S$^9$ (in which EDTA was used) with C$^+$ (in which no treatment was performed, and only tap water spray was used) showed a spectacular finding that SFE level in EDTA containing surfactant/coolant solutions is near the group C$^+$ with no significant difference. In other words, C$^+$ and groups S$^7$-S$^9$ are placed in the same subset (Table 4). The levels of SFE in groups S$^7$, S$^8$ and S$^9$ are more than group C$^-$ in which 37% phosphoric acid for 10 seconds was used with a significant difference (Table 4). Acid etching solves and removes all minerals and considerably reduces SFE. The higher level of SFE in group S$^7$ compared to S$^2$ can be attributed using EDTA in S$^7$ and its resultant minerals which make a complex with high energy level. This can reconcile with SFE level when surfactant/coolant solutions do not have EDTA (S$^1$-S$^5$). In such case, the mineral/organic ratio of the surface increases and consequently causes a rise in SFE. S$^7$ caused the highest SFE (76.97 mj/m$^2$) among all testing groups ($S^1$-$S^9$) with HLB=7 and CMC=0.5%. The value of HLB in $S^7$ represents the "wetting and spreading agents" and the CMC=0.5% as well as the concentration of EDTA in $S^7$ approve the results. See Tables 2 and 4.

In SEM evaluations, $S^2$ and $S^7$ had a similar potential in removing the smear layer. It indicated that adding EDTA may not significantly influence smear layer removal of $S^2$. But, their values of SFE in conjunction with the SEM results strongly confirmed that $S^7$ can remove smear layer without reduction of SFE, which is usually happened in total-etch approach.

Study 1: Conclusion: The following results were shown:
(1) Acid etching thoroughly removes the smear layer and dramatically decreases SFE up to 57.85 mJ/ $m^2$.
(2) Using surfactant /coolant solutions with or without EDTA remove the smear layer within the same range while SFE is higher in groups with EDTA ($S^7$-$S^9$) than in groups without EDTA ($S^1$-$S^6$).
(3) Using surfactant /coolant solutions without EDTA in groups $S^1$-$S^6$ remove the smear layer and provide a dentinal SFE to the level of group $C^-$ (etching with 37% phosphoric acid for 10 seconds that is seen in conventional total etch approach), which is clinically acceptable.
(4) Using surfactant /coolant solutions with EDTA in groups $S^7$-$S^9$ removes the smear layer and increases the SFE to the level of group $C^+$ which is significantly higher than the clinically acceptable level which is seen in conventional total etch approach.
(5) Groups $S^7$ (76.9 mJ/$m^2$) in CMC=0.5% and HLB=7 and group $C^+$ (72.82 mJ/$m^2$) showed the highest levels of SFE with no significant difference but, with a significant difference in smear layer removal potential ($S^7$>$C^+$).
(6) The proper washing time after cutting, in this study, is not still known.

Study 2: Determining Appropriate Washing Time in Terms of SFE (E): The aim of this study was to determine the appropriate washing time after using $S^7$ as a coolant, in terms of SFE.

Twenty-five carries free premolars were placed in 5 experimental groups, five in each randomly. First, they were cut using high-speed handpiece and long diamond fissure bur to get an appropriate flat dentinal surface in buccal surfaces for measuring contact angles (primary cutting). To simulate real cutting manner, dentinal surfaces were cut again using high-speed hand piece with a new long diamond fissure bur for 5 seconds while defined coolant ($S^7$ and tap water) was sprayed for each group (secondary cutting). In the positive control group (group1), Conventional Cutting (CC) was done using tap water as a coolant, without etching, and 15-seconds rinsing time with air-tap water and then drying (E-CC). In the negative control group (group 2), Conventional Cutting (CC) was done using water as a coolant, and then etching (E) with 37% phosphoric acid for 10 seconds (E-CCE). Rinsing and drying were done as the same as group 1. In the other three testing groups, cutting was done using $S^7$ surfactant/coolant solutions from study 1 with CMC=0.5% and HLB=7, (Tables 1 and 2) as a coolant to obtain the same flat surfaces, with 5, 10 and 15 seconds rinsing times (with tap water spray) thereafter respectively (E-C5, E-C10, and E-C15) and drying step was done as the same as groups 1&2. SFE measurement was done as the same way as in Study 1.

Duncan tests between all groups shows that group 1 (E-CC) placed in high energy subset (p-value=0.000) and group 2 (E-CCE) placed in low energy subset (p-value=0.000) and testing groups (E-C5, E-C10, and E-C15) were located between these two groups (p-value=0.116). However, there is a little difference between testing groups (Sig.=0.013) in term of SFE. Moreover, T-test between E-CC and E-C5 groups shows that there is no significant difference (Sig=0.678) in terms of SFE. In addition, considering the Duncan test between all groups, it can be expressed that except group2 (E-CCE), other groups could be placed in a same statistical subset with a high SFE level. It means that using $S^7$ as a coolant solution (in testing groups) with 5-minute washing time causes the level of SFE as high as the SFE level in cutting dentin without etching (E-CC) that is significantly higher than group2 (E-CCE), which uses an acid etch technique.

Study 2: Conclusion: The optimum washing time, in terms of SFE, in testing groups (using $S^7$ as a coolant) is 5 seconds (E-C5), which is 10 seconds less than the washing time in conventional total-etch approach (E-CCE), while the SFE is at the same level of E-CC but without the destructive presence of the smear layer. It also confirmed the result of Study 1.

Study 3: Determining Appropriate Washing Time in Terms of Bond Strength (B): The aim of this study was to determine the appropriate washing time when using $S^7$ as a coolant, in terms of bond strength using total-etch and self-etch bonding agents.

Ninety-six premolar teeth were randomly divided into 8 groups with twelve samples in each. First, they were cut using high-speed handpiece and long diamond fissure bur to get an appropriate flat dentinal surface in buccal surfaces (primary cutting). To simulate real cutting manner, dentinal surfaces were cut again using high-speed hand piece with a new long diamond fissure bur for 5 seconds while defined coolants ($S^7$ and tap water) were sprayed for each group (secondary cutting). In groups 1 and 2, tap water coolant was used. Excite® (total-etch), (E) and Adhese® (self-etch), (A) bonding agents were used respectively as the manufacturer's instruction. In the other groups, surfactant/coolant solution ($S^7$) was used as a coolant. Washing times in groups 3, 4, and 5, were 5, 10 and 15 seconds (with tap water spray) respectively and Excite® was applied without etching step. Washing times in groups 6, 7 and 8, were 5, 10 and 15 seconds (with tap water spray) respectively and Adhese® was applied to the manufacturer's instruction. Then, a 2×2 composite cylinder was placed using a polyethylene mold and cured for 40 seconds with 400 mW/$cm^2$ in all prepared samples. After ×500 thermocycling, shear bond strength was tested. The data were analyzed using One-way ANOVA, Duncan, and T-test. See Table 5 below.

TABLE 5

| Group number | Coolant | Etching | Washing time (Seconds) | Adhesive | Abbreviation |
|---|---|---|---|---|---|
| 1 | Tap water spray | Yes | 15 | Excite ® | B-CCE |
| 2 | Tap water spray | No | 5 | Adhese ® | B-CCA |
| 3 | $S^7$ spray | No | 5 | Excite ® | B-C5E |
| 4 | $S^7$ spray | No | 10 | Excite ® | B-C10E |
| 5 | $S^7$ spray | No | 15 | Excite ® | B-C15E |
| 6 | $S^7$ spray | No | 5 | Adhese ® | B-C5A |
| 7 | $S^7$ spray | No | 10 | Adhese ® | B-C10A |
| 8 | $S^7$ spray | No | 15 | Adhese ® | B-C15A |

The best washing time was found to be 5 seconds in terms of shear bond strength for both bonding systems.

Using the composition of the present disclosure together with the conventional total-etch bonding system, the etching step (which lasts 15 seconds for etching and 15 seconds for washing) can be deleted which means at least 25 seconds time-saving in total, because it has removed the smear layer already at the same time of cutting and just need 5 seconds washing time right after. In addition, this alternative approach leads to bond strength like the conventional approaches as well.

Using the composition of the present disclosure together with the conventional self-etch approach, the quality of bonding, through removing the smear layer barrier, can be improved too. Moreover, this approach possibly saves more time because it has removed the smear layer already at the same time of cutting and no need for more waiting time for the bonding agent to penetrate well.

Persons of ordinary skill in the art may appreciate that numerous design configurations may be possible to enjoy the functional benefits of the inventive systems, which increases the SFE while producing the same range of bond strength for total-etch and self-etch bonding systems. Thus, given the wide variety of configurations and arrangements of embodiments of the present invention the scope of the invention is reflected by the breadth of the claims below rather than narrowed by the embodiments described above.

What is claimed is:

1. A multifunctional dental coolant comprising, based on a batch having a total volume of 1000 cc:
   1.07 g polyoxyethylene sorbitan monooleate;
   3.93 g sorbitan monooleate;
   0.05M ethylene diamine tetra acetic acid (EDTA);
   0.025 g sodium benzoate; and
   distilled water in a volume sufficient for reaching the total volume of 1000 cc.

* * * * *